United States Patent [19]

Flint

[11] Patent Number: 4,490,391

[45] Date of Patent: Dec. 25, 1984

[54] COMPOSITION FOR SHOCK TREATMENT

[76] Inventor: John E. Flint, R.R. 2, Charles City, Iowa 50616

[21] Appl. No.: 521,149

[22] Filed: Aug. 8, 1983

[51] Int. Cl.³ ............................................ A61K 31/19
[52] U.S. Cl. .................................................... 424/317
[58] Field of Search ........................................ 424/317

[56] References Cited

U.S. PATENT DOCUMENTS

| | | | |
|---|---|---|---|
| 2,217,905 | 10/1940 | Hoffman et al. | 424/146 |
| 2,276,234 | 3/1942 | Jones | 424/317 |
| 2,946,722 | 7/1960 | Hoffman et al. | 424/317 |
| 3,228,831 | 1/1966 | Nicholson et al. | 424/317 |
| 3,356,570 | 12/1967 | Butch | 424/317 |

OTHER PUBLICATIONS

Merck Index 7th Ed. (1976) pp. 1107+1120.

*Primary Examiner*—Stanley J. Friedman
*Attorney, Agent, or Firm*—Zarley, McKee, Thomte, Voorhees & Seas

[57] ABSTRACT

A treating composition and method for treatment of shock and/or stress in animals. The composition comprises, in a preferred form, equal volume amounts of solutions of sodium acetate and sodium propionate. It may be administered orally, intravenously, subcutaneously, etc. The preferred dosage level is from about 0.25 cc. per pound of body weight to about 0.5 cc. per pound of body weight.

7 Claims, No Drawings

COMPOSITION FOR SHOCK TREATMENT

BACKGROUND OF THE INVENTION

Domestic animals, such as cows, calves, pigs, horses, dogs, cats, etc. all are susceptible to shock or stress caused from nutritional deficiencies, trauma, infection or extreme environmental changes such as lot adaptation stress in cattle. While such stress does not necessarily exhibit its most extreme form in shock in all cases, it nevertheless adversely affects the animal. This is particularly important with cattle, calves, cows, pigs, piglets and sows. These latter animals are all meat sources and undergoing stress they often will not eat as they should, or in any event, their weight gain is not as fast as it should be, resulting in an economic loss to the producer. Then too, stress also makes domestic livestock susceptible to numerous other infections etc.

Accordingly, there is a real and continuing need for an inexpensive shock and/or stress treatment to give domestic animals an immediate boost responsive to shock and/or stress.

The primary objective of the present invention is to fulfill the above need with both a composition and method for counteracting stress and/or shock in domestic livestock animals, and other animals as well.

SUMMARY OF THE INVENTION

The present invention relates to a composition for treating shock and/or stress in animals, most commonly domestic livestock animals, but including other lower animals and human beings as well. The composition is a combination of small but effective amounts of solutions of sodium acetate and sodium propionate.

DETAILED DESCRIPTION OF THE INVENTION

The treating compositions of this invention, designed for treating shock or stress in animals, comprise an admixture of a solution of a small but effective amount of sodium acetate with a solution of a small but effective amount of sodium propionate.

The concentrations of each of the solutions may vary, but generally satisfactory results are obtained when the concentrations are within the range of from about 0.5% by weight concentration to about 12.5% by weight concentration, preferably from about 1.8% by weight concentration to about 12.5% by weight concentration.

While the volume of each solution at the concentrations specified may vary within the range of from about one-half to about twice as much as the other, it is preferred that about equal volume amounts of each be employed. When equal amounts are employed, the best results are obtained.

The pH of the solution is not a critical factor, and the pH ordinarily does not need to be adjusted beyond the pH as it exists in the combined solutions. Generally, however, it should be within the range of from about 7.2 to about 8.0. The preferred solution is a saline solution.

The dosage level may vary over some range, from about 0.25 cc/lb. to about 5 cc/lb, but has generally been found to be satisfactory, for the concentration specified herein, if the dosage amount is from about 0.25 cc. per pound of body weight to about 0.5 cc. per pound of body weight. The most preferred dosage level is from about 0.3 cc per pound of body weight to about 0.4 cc per pound of body weight. The dosage levels and the concentrations should not be in excess of those specified herein or the life of the animal may be in danger. If in doubt, the dosage levels should be used at the lower ends of the ranges specified.

The composition may be administered in the conventional fashions, including intravenously, subcutaneously, orally or intraperitoneally. Intravenous administration is perhaps the most effective. It may even be administered topically in wound ointments, creams, salves and lotions.

The number of administrations will necessarily vary depending upon the conditions of the shock and/or stress found in the animal. But generally a single administration is sufficient to counteract normal livestock stress. For small calves in very weakened condition, two to three days of oral administration will noticeably improve them.

Within hours after treatment of all types of animals, one observes rising blood pressure, the animal becomes more alert, the animal's gum color is improved, particularly for cattle the color of the blood becomes much brighter, the animal's coat will become shinier in two to three days, and if the animal is shivering at the time of treatment, the shivering will notably quit within moments. All of these observable factors tend to show that the treating composition is immediately effective in reducing stress or shock.

The composition appears to be synergistic, in that the same result is not achieved when a sodium acetate solution, at the concentration specified, is used alone; nor, is the effect achieved when a sodium propionate solution is used alone.

While the above description has been given with regard to the combination of sodium salts of acetate and propionate, it should be understood that sodium salts are preferred only. Other water soluble alkali and alkali metal salts of acetic acid and propionic acid can also be employed. For example, one may use ammonium salts, potassium salts, calcium salts, etc.

While the specific physiological effect of the present composition is not known with assurance, and while the applicant does not wish to be bound by any theory of the precise biological changes which occur, it is believed that the composition itself acts as a driving force to positively drive the Krebs' cycle reaction in a manner favorable to the animal's biological system. It should be emphasized that the composition is not a cure for any specific disease, but simply provides a significant boost to the animal in terms of its own biological system performance.

The following examples are offered to further illustrate, but not limit, the process and product of the invention.

EXAMPLES

Example 1

A 13 year old, spayed, female collie weighing 55 pounds was presented for the removal of skin tumors from the chin and one front leg. Six months previously she was operated on two days in a row with no complications. She was given a routine dose of glycopyrrolate and xylazine but soon became too depressed with a weak pulse and very pale mucus membranes. She was given 15 cc of a 12½% solution of Na acetate and Na propionate intravenously. Her pulse pressure rose quickly, her mucus membranes became pink and her pain reflexes returned within a minute or two. The surgery was completed quickly with some local anesthesia. The patient seemed to be getting into trouble with the anesthesia for which there is no specific antidote. The acetate and propionate coorrected the problem almost immediately and the patient awoke from the anesthesia faster than normal.

Example 2

A Holstein cow which had calved the day before, was reported to be listless and had no appetite and had some blood in otherwise normal milk. At the time of the examination the cow breathed a little fast, had a rapid heart rate, had normal, thick mucus in the cervix, a large but normal feeling udder with normal appearing milk and a moderate smell of ketones on her breath. Her rectal temperature was 106.8° F. A blood sample was taken for examination. That examination revealed a blood glucose level of 25 mg per 100 ml, a packed cell volume of 33% with slight icterus, a plasma pH of 6.8 and a total plasma protein of 9.8 gm per 100 ml of blood.

A diagnosis of septicemia was made and she was given 3000 cc of 2% Na acetate and Na propionate plus 500 cc of 50% dextrose intravenously. She was also given neomycin, penicillin, and streptomycin intramuscularly. While the fluid was being given, the odor of ketones almost disappeared from the cow's breath. Treatment was finished about 11:30 A.M. so the cow was let out to pasture for the day. She only laid about the barnyard for a day. At milking time in the evening her rectal temperature was 102° F.

The next morning she ate a little of her grain, her temperature was 101.8° F., the mucus membranes had good color, the milk appeared normal, the udder was less swollen and softer but the rumen was inactive. Blood was taken for examination. The blood glucose was 25 mg per 100 ml, the packed cell volume was 35% with slight icterus, the plasma pH was 6.8, and the total protein was 9.2 gm per 100 ml. The cow was given a large dose of magnesium hydroxide via stomach tube and antibiotic intramuscularly. The cow appeared much improved and was turned out to pasture. She proceeded to walk ¼ mile through a stream and over a hill to join the grazing herd. She was given antibiotics intramuscularly for two days as she completed her recovery.

In the past, the same therapy was used in similar situations with the exception of using sodium bicarbonate intravenously at a dosage of 2.5 mEq per pound of body weight instead of the acetate and propionate of the invention. The plasma pH would have changed to a normal 7.0 and the total protein level would have lowered somewhat close to a more normal 7.0 but the patient wouldn't usually respond as well as this cow, treated with the invention.

Example 3

A mature sow which had farrowed 12 live pigs the day before was the patient. She cleaned up her feed in the morning but by early afternoon she was listless and had a rectal temperature of 106° F. Also, the pigs were looking and acting hungry. She was given 1000 cc of 2% acetate and propionate subcutaneously plus neomycin, erythromycin and oxytocin intramuscularly. She was up and passed some hard feces while being treated. At about 9:00 P.M. she appeared to be in distress and vomited. Her rectal temperature was 104° F. and she seemed to be improved and had milk in her udders when examined at 10:00 P.M. The pigs appeared more satisfied too.

The next day at noon her rectal temperature was 103° F. which was normal in the farrowing house at that time. She had not eaten, but she was drinking and her pigs appeared satisfied. She was given erythromycin.

By the third day the sow was eating and all twelve of her pigs appeared to be gaining weight. She was given no further treatment.

Each day, before treatment, a blood sample was taken from the sow. It was analyzed and the results are tabulated below.

|  | Blood Glucose (mg per 100 ml.) | Packed Cell Volume percent) | Plasma pH | Total Plasma Protein (gm per 100 ml) |
|---|---|---|---|---|
| Day 1 | 45 | 42 hemolysis | 6.8 | 9.2 |
| Day 2 | 25–45 | 36 slight hemolysis | 7.0 | 9.2 |
| Day 3 | 45 | 32 clear | 7.0 | 10.0 |

The sow made a very nice recovery and the condition of the pigs indicates that the milk flow increased faster than it did with other treatment regimens previously used.

Example 4

An eight pound, male, long haired domestic cat was presented with feline urinary syndrome (plugged urethra and a very full, tense bladder). The cat was uncomfortable but alert. The bladder was easily drained by backflushing the urethra with lidocaine solution and manually expressing the bladder. The cat proceeded to depression and shock. An intravenous catheter was inserted into a jugular vein through a cutdown incision. There was no hemorrhage due to low blood pressure.

The cat was prepared for treatment for shock, uremia and an expected diuresis. A continuous drip of Lactated Ringer's solution was started. To this was added 20 mEq Na bicarbonate as a 1.4% solution, 4 units of regular insulin with 16 cc of 50% dextrose and 35 cc of a 0.9% Na acetate and 0.9% Na propionate solution. Antibiotic was given intramuscularly. The drip was started about noon and continued through the night. The bladder was emptied manually two or three times during the first day.

The first liter of Ringer's and the other fluids were all in the cat by midmorning of the second day. The cat felt better and leaked urine but couldn't empty his bladder. The cat was anesthetized in the afternoon and a urethral catheter was sutured in place. Approximately 200 cc of blanced electrolyte and 12 cc of 1.8% acetate and propionate solution were given subcutaneously at this time.

The second night and third day were uneventful. The cat passed urine and feces and begin to use the litter box. During the third day, the cat removed the urinary catheter. He was still depressed and wouldn't eat on the fourth morning. He made a remarkabe recovery when the owner came for him so he went home with antibiotic and urinary acidifier.

Until adding the acetate and propionate to the treatment, these cases had to stay on an intravenous drip for two or three days with as much as 2000 cc of Lactated Ringer's during the first 24 hours.

Example 5

A twelve or thirteen year old, mixed female dog weighing eleven pounds was presented for the removal of mammary tumors and an ovariohysterectomy. She had one tumor about a centimeter in diameter and twelve or thirteen like grains of sand. Four years ago, other mammary tumors had been removed from this same dog. She was anesthetized with glycopyrrolate, xylazine and ketamine. She jumped and not all of the ketamine went into the dog. Twenty four cubic centimeters of 2% acetate and propionate were given subcutaneously and pentabarbital sodium was given intravenously to effect. Preoperative and postoperative blood samples were taken and analyzed. The results are tabulated below:

|  | Blood glucose (mg per 100 cc) | Packed Cell Volume (percent) | Plasma pH | Total Plasma Protein (gm per 100 cc) |
| --- | --- | --- | --- | --- |
| preop. | 45 | 43 | 7.0 | 8.6 |
| postop. | 130 | 35 | 7.0 | 7.5 |

At the completion of surgery, the dog had cold skin and low pulse pressure but good mucus membrane color and good reflexes. The dog was up, alert and apparently feeling fine the day after surgery.

Example 6

An adult Holstein milking cow with dyspnea and a fever was treated. She had been purchased about four days previously with a mild case of mastitis. At the morning milking, she had a mild fever of 103° F. By midmorning it was up to 104° F. At 2:30 or 3:00 P.M., her temperature was 106° F. I diagnosed the problem as a septicemia, probably related to the mastitis. I gave her 3000 cc of 8⅓% dextrose and 3000 cc of 2% acetate and propionate intravenously through a 12 gauge needle. That took twenty to thirty minutes. During that time her breathing eased a little, her oral mucus membranes became pink and the skin of the teats changed from pale to a normal pink color. At the end of the treatment, her rectal temperature was 102° F. She was given antibiotics then and for another two days. She made an uneventful recovery. The true etiology of her problem is still unknown, but the rapidity with which her fever subsided is remarkable in comparison with past treatments.

Example 7

The patient was a sow which had farrowed about 36 hours before. Her rectal temperature was 103° F. which was normal for sows in this farrowing house on that day. She was weak and had to be helped up. The last three mammary glands on the right side were swollen and hard. One of the three glands was becoming necrotic where the pressure of a pig laid upon had apparently cut off the circulation in the infected gland. There was a slightly purulent vaginal discharge and vaginal bruising. It was diagnosed that she had acute, toxic mastitis, with or without vaginitis.

Treatment consisted of 1000 cc of 2% acetate and propionate solution subcutaneously chlorhexidine suspension in the vagina and neomycin, erythromycin and oxytocin intramuscularly.

After treatment she was helped up and she drank quite a lot of water. The owner put the pigs back with her later and reported that by 2:00 A.M. she was stronger and could get up and down to drink. The next morning the sow had relapsed a little but the litter appeared to be getting fed. Antibiotics were continued for a few days. Phosphate was given for a few days to keep her blood sugar up and she and the litter progressed satisfactorily.

In the past, this type of case has usually ended with the loss of most or all of the pigs and maybe even the death of the sow after several days of more rigorous treatment.

What is claimed is:

1. A method of treating shock and/or stress in animals comprising:
   administering to said animal a small but shock treating effective amount of a composition comprising an admixture of solutions of sodium acetate and sodium propionate each of said solutions having a concentration of from about 0.5% by weight to about 12.5% by weight, respectively, of sodium acetate and sodium propionate.

2. The method of claim 1 wherein said administration is intravenous administration.

3. The method of claim 1 wherein said administration is subcutaneous administration.

4. The method of claim 1 wherein said administration is oral administration.

5. The method of claim 1 wherein said administration is intraperitoneal administration.

6. The method of claim 1 wherein the dosage amount is 0.25 cc per pound of body weight to about 0.5 cc per pound of body weight.

7. The method of claim 6 wherein the dosage amount is from about 0.3 cc per pound of body weight to about 0.4 cc per pound of body weight.

* * * * *